United States Patent
Kumagai (12)
(10) Patent No.: US 6,656,511 B1
(45) Date of Patent: Dec. 2, 2003

(54) CALCIUM SORBEFACIENTS AND PROCESS FOR PRODUCING THE SAME

(75) Inventor: Hitomi Kumagai, Tokyo (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 10/149,118

(22) PCT Filed: Aug. 29, 2000

(86) PCT No.: PCT/JP00/05837

§ 371 (c)(1),
(2), (4) Date: Jun. 7, 2002

(87) PCT Pub. No.: WO01/41777

PCT Pub. Date: Jun. 14, 2001

(30) Foreign Application Priority Data

Dec. 9, 1999 (JP) .......................................... 11-350283

(51) Int. Cl.[7] .............................................. A61K 35/78
(52) U.S. Cl. ....................................... 424/757; 424/439
(58) Field of Search ................................ 424/757, 439

(56) References Cited

FOREIGN PATENT DOCUMENTS

| JP | A 7-227215 | 8/1995 |
|---|---|---|
| JP | A 7-228540 | 8/1995 |

OTHER PUBLICATIONS

Kumagai et al., "Influence of Phytate Removal and Structural Modification on the Calcium–binding Properties of Soybean Globulins", Biosci. Biotechnol. Biochem, pp 341–346, 1998 vol. 62, No. 2.

Kumagai et al. "Preparation of Phytate–Removed Deamidated Soybean Globulins by Ion Exchangers and Characterization of Their Calcium–Binding Ability", J. Agric. Food Chem., pp. 172–176, 2002 (Published on Web Nov. 21, 2001).

Kumagai, H., for the Japanese Society for Food Science and Technology 46th Conference, Sep. 6, 1999 w/ abstract.

*Primary Examiner*—Francisco Prats
*Assistant Examiner*—Susan D. Coe
(74) *Attorney, Agent, or Firm*—Oliff & Berridge, PLC (57) ABSTRACT

There are provided a calcium absorption enhancing agent produced by subjecting a vegetable protein to at least a treatment of removing a phytate with an anion exchange resin and a deamidation treatment with a weakly acidic cation exchange resin, and a method for producing it.

Thereby, calcium absorption enhancing agents which can be widely applied and excellent in processability can be obtained.

34 Claims, 4 Drawing Sheets

CALCIUM SORBEFACIENTS AND PROCESS FOR PRODUCING THE SAME

TECHNICAL FIELD

The present invention relates to a calcium absorption enhancing agent and a method for producing it.

BACKGROUND TECHNOLOGY

According to the National Nutrition Survey, an average of Japanese daily calcium intake is still lower than the recommended daily amount. Moreover, a disease resulting from calcium deficiency such as osteoporosis or the like is becoming one of the serious adult diseases. Therefore, it is an important subject for maintaining health of Japanese people to increase calcium intake.

For this purpose, various calcium preparations have been developed. For example, there have been developed calcium preparations containing powder produced by grinding bone of a fish or an animal, egg shell, shell or the like; a calcium salt, or the like, as well as calcium enriched foods to which one or more of the above-mentioned calcium preparations are added, which are commercially available.

However, since the amount of calcium absorption in intestines is small, it is not enough to take calcium. Therefore, it is desired to develop a calcium absorption enhancing agent for accelerating calcium absorption. It is supposed that a substance which weakly binds to a large amount of calcium, and prevents it from precipitating in intestines and being excreted without being absorbed may be effective as a substance for accelerating calcium absorption in intestines.

Casein phosphopeptide (CPP) is known as such a substance. CPP is a substance generated in a process of digestion of casein which exists in cow's milk. Sour milk beverages to which CPP is added as a calcium absorption enhancing agent have been developed, and are marketed.

However, since CPP is a peptide originating from cow's milk, it has a so-called cow's milk flavor. Furthermore, it has poor processing characteristics, and is hardly applied to products other than dairy products such as sour milk beverages. Accordingly, there is a problem that a person who hardly drinks cow's milk and sour milk beverages cannot take it. It has been desired strongly to develop a calcium absorption enhancing agent which can be applied to a still wider scope of products.

From such a view point, calcium absorption enhancing agents other than CPP have been studied, and soybean protein has been proposed as one of them. However, it has been reported that although a soybean protein has high affinity for calcium, a calcium absorption enhancing effect thereof in vivo is low (Br. J. Nutr., 43, 457–467, 1980; J. Nutr. Sci. Vitaminol., 32, 67–76, 1986). It may be because phytic acid binding to soybean protein may bind to calcium in a digestive tract, to form a water insoluble salt which cannot be absorbed from intestinal wall.

Not only soybean protein, but other vegetable proteins such as proteins of legumes, cereals or the like contain a large amount of acidic amino acids which can bind to calcium weakly. Accordingly, they also seem to be desirable as a calcium absorption enhancing agent. However, a calcium absorption enhancing effect thereof is not high in vivo. One of the reasons may be that many of the acidic amino acids exists as an acid amide form, which cannot bind to calcium as it is.

The inventor of the present invention has noticed that it is advantageous to remove phytic acid and to remove amino groups of acid amide groups in advance, to improve calcium absorption enhancing effect, when using vegetable protein such as soybean protein as a raw material of a calcium absorption enhancing agent, and has developed a soybean protein wherein phytic acid is removed with an anion exchange resin and deamidation is achieved with an enzyme (H. Kumagai et al. Biosci. Biotechnol. Biochem., 62 (2), 341–346, 1998).

However, cost of the deamidation of soybean protein with enzyme is high, and the amount of amide which can be removed is only about 80 $\mu$mol/g, which is not enough. The inventor of the present invention has studied further, and found that when the deamidation treatment of vegetable protein was performed using weakly acidic cation exchange resin, deamidation can be performed very efficiently. Thereby, the present invention has been completed.

DISCLOSURE OF THE INVENTION

The present invention provides the following calcium absorption enhancing agents.

(1) A calcium absorption enhancing agent produced by subjecting a vegetable protein to at least a treatment of removing a phytate with an anion exchange resin and a deamidation treatment with a weakly acidic cation exchange resin.

(2) The calcium absorption enhancing agent of (1) wherein the vegetable protein is a soybean protein.

(3) The calcium absorption enhancing agent of (1) wherein the deamidation treatment with the weakly acidic cation exchange resin is conducted at a temperature in the range of 0–50° C.

(4) The calcium absorption enhancing agent of (2) wherein the deamidation treatment with the weakly acidic cation exchange resin is conducted at a temperature in the range of 0–50° C.

(5) The calcium absorption enhancing agent of (1) wherein the weakly acidic cation exchange resin has carboxyl groups as an exchange group.

(6) The calcium absorption enhancing agent of (2) wherein the weakly acidic cation exchange resin has carboxyl groups as an exchange group.

(7) The calcium absorption enhancing agent of (3) wherein the weakly acidic cation exchange resin has carboxyl groups as an exchange group.

(8) The calcium absorption enhancing agent of (4) wherein the weakly acidic cation exchange resin has carboxyl groups as an exchange group.

Moreover, the present invention relates to the following method for producing a calcium absorption enhancing agent.

(9) A method for producing a calcium absorption enhancing agent wherein a vegetable protein extracted from a plant is subjected to at least a treatment of removing a phytate with an anion exchange resin and a deamidation treatment with a weakly acidic cation exchange resin.

(10) The method for production of (9) wherein the deamidation treatment with the weakly acidic cation exchange resin is conducted at a temperature in the range of 0–50° C.

Moreover, the present invention relates to the following calcium enriched foods, the following nutrition compositions for calcium enrichment, and the following pharmaceuticals.

(11) A calcium enriched food which contains the calcium absorption enhancing agent of (1).

(12) A calcium enriched food which contains the calcium absorption enhancing agent of (4).

(13) A calcium enriched food which contains the calcium absorption enhancing agent of (6).

(14) A nutrition composition for calcium enrichment which contains the calcium absorption enhancing agent of (1).

(15) A nutrition composition for calcium enrichment which contains the calcium absorption enhancing agent of (4).

(16) A nutrition composition for calcium enrichment which contains the calcium absorption enhancing agent of (6).

(17) A pharmaceutical preparation which contains the calcium absorption enhancing agent of (1).

(18) A pharmaceutical preparation which contains the calcium absorption enhancing agent of (4).

(19) A pharmaceutical preparation which contains the calcium absorption enhancing agent of (6).

BEST MODE FOR CARRYING OUT THE INVENTION

In this specification, "vegetable protein" means a substance containing an increased amount of protein obtained by processing plants such as seeds for harvesting oils or the same which is defatted, legumes, cereals or the like.

The above-mentioned vegetable protein may be in the form of powder, grain, paste, fiber or the like.

Examples of the seeds for harvesting oil include: a sunflower, a rapeseed, a sesame, a peanut, an almond, a walnut and the like.

Examples of legumes include: a soybean, an azuki bean, a cowpea, a broad bean, a green bean, a chick pea, a green gram, a lima bean and the like.

Examples of cereals include: wheat, corn, rice, oats, burley, buckwheat, millet, pigeon wheat, barnyard grass, foxtail millet, rye wheat, and the like.

The vegetable protein is preferably soybean protein. In this specification, "soybean protein" means the protein extracted from soybean, including not only those purified to be almost pure, but also those wherein protein content is raised to a certain extent by treatment, such as defatting, extraction with water, or the like, for example, defatted-soybean powder, concentrated soybean protein, separated soybean protein, or the like.

The protein content of the vegetable proteins is preferably in the range of 20 to 100%.

Treatment for obtaining the vegetable protein used for the present invention may consist of a combination of steps such as dehulling, grinding, defatting, extraction with water, acid precipitation, washing, centrifugation, dialysis, and drying, depending on the kind of plants used as a raw material. Each steps can be performed by a method which is commonly conducted as for each plant.

Soybean protein can be extracted, for example, by performing each step of dehulling, grinding, defatting, extraction with water or a buffer solution, acid precipitation, centrifugation, dialysis, and lyophilization, one by one.

In this specification, "the treatment of removing phytate with the anion exchange resin" means removing phytic acid or salts thereof binding to vegetable protein by contacting the vegetable protein to an anion exchange resin.

The treatment of removing phytate with anion exchange resin is performed, for example, by mixing the vegetable protein with anion exchange resin for a predetermined time at suitable pH and temperature in water or a suitable buffer solution, for example, a Tris-HCl buffer solution or a phosphoric acid buffer solution. Then, the ion exchange resin is removed by filtration and the treated protein can be extracted from the filtrate by a treatment such as dialysis, vaporization, drying, or the like.

The anion exchange resin to be used can be those having —$N^+(CH_3)_3$ or —$N^+(C_2H_4OH)$ $(CH_3)_2$ as an exchange group, and with an ion exchange capacity of, for example, 0.7–1.5 g Eg/ml humid resin.

Treatment time may be in the range of from 5 minutes to 10 hours, preferably from 5 minutes to 5 hours, especially from 5 minutes to 3 hours.

Treatment temperature is, preferably in the range of 0 to 70° C., especially 0 to 50° C. When the treatment temperature is high, hydrolysis of the protein will be progressed, and taste and processability will be lowered.

Although pH is not limited, it can be, for example pH 6 to 8.

Although an amount of the anion exchange resin to be used is not limited, it can be, for example, in the range of 0.1 to 50 g, preferably 1 to 10 g per 100 ml of a 0.1–5% protein solution.

In this specification, "deamidation treatment with weakly acidic cation exchange resin" means contacting vegetable protein to a weakly acidic cation exchange resin to remove amino groups from acid amide groups of amino acids which constitute the vegetable protein, to provide free carboxyl groups.

The deamidation treatment with weakly acidic cation exchange resin is performed, for example, by mixing vegetable protein with weakly acidic cation exchange resin, for a predetermined time, at suitable pH and temperature in water or a suitable buffer solution, such as a Tris-HCl buffer solution, a phosphoric acid buffer solution or the like. Then, the ion exchange resin is removed by filtration, and the treated protein can be extracted from the filtrate by a treatment such as dialysis, drying, or the like.

As the weakly acidic cation exchange resin, there can be used those having, for example, —COOH and —N(CH$_2$COOH)$_2$ as an exchange group, and with ion exchange capacity of, for example, 0.5–5 gEq/l humid resin.

Treatment time may be in the range of 30 minutes to 15 hours, preferably 1 to 10 hours, especially 3 to 6 hours.

Treatment temperature is in the range of 0 to 70° C., more preferably 0 to 50° C. When the treatment temperature is too high, hydrolysis of the protein is advanced, and taste and processability thereof is lowered.

Although pH for the treatment is not limited, it can be, for example pH 6 to 8.

Although an amount of the weakly acidic cation exchange resin to be used is not limited, it can be in the range of, for example, 1 to 100 g, preferably 10 to 50 g, per 100 ml of 0.1 to 5% of a protein solution.

The protein may be subjected to the treatment of removing phytate with anion exchange resin, after subjected to the deamidation treatment with the weakly acidic cation exchange resin. Alternatively, the protein may be subjected to the deamidation treatment by the weakly acidic cation exchange resin after subjected to the treatment of removing phytate with the anion exchange resin.

The present invention provides a calcium enriched food, feeds, a nutrition composition for calcium enrichment, and pharmaceuticals, which contain the above-mentioned calcium absorption enhancing agent, preferably together with a calcium agent.

As the calcium agent, these can be used powder obtained by grinding bone of fish or animal, egg shell, shell, or the like; calcium salts, such as calcium chloride, calcium carbonate, calcium lactate, calcium gluconate, and calcium phosphate.

The above-mentioned calcium enriched food may be food in any form, for example, it can be in the form of a solid, a gel, a liquid or the like. It can be, for example, meat products; fish paste products; daily dishes; frozen food; a soybean processed food such as tofu; drinks such as soy milk, fermented milk and soft drinks; confectionery such as jellies, pudding, a biscuit, a wafer, a rice cracker, and a candy, and seasonings such as miso, soy sauce, or the like.

In production of these calcium enriched foods, the calcium absorption enhancing agent can be added in a suitable step of production of each food.

Since soybean protein functions also as a gelatinizer, it can be added in a gelation process in the case of using soybean protein.

The above-mentioned nutrition composition for calcium enrichment and the pharmaceuticals may further contain other nutrients, such as a sugar, a lipid, vitamins, and minerals. Moreover, proteins originating from other material such as milk protein, may be included therein.

The above-mentioned nutrition composition for calcium enrichment and pharmaceuticals may be in any form, such as a tablet, a granule, powder, a capsule, solution, a health drink, and syrup. It can contain adjuvants, such as excipients such as an extender, a diluent, a solvent and a bulking agent; a solubilizing agent; an emulsifier; a suspending agent; a dispersant; a binder; a lubricant; a coating agent; a gradual releasing agent; an anti-oxidant; preservatives; a brightener; a sweetener; a colorant; a flavoring agent; or the like.

EXAMPLE

The present invention will be further explained by the following Examples. All rates and percentages are based on weight, unless otherwise specified. These examples are only for illustration, and do not limit the scope of the present invention. The skilled in the art can make any improvements or modifications according to the information obtained from the description or the information known in the art.

Example 1

(1) Extraction of soybean protein

Soybeans as a raw material were dehulled, ground with a mixer, and defatted with 5 times weight of hexane. The defatted soybeans were stirred for one hour with 20 times weight of 0.03 M Tris-HCl buffer-solution (pH 8.0) containing 0.01 M of 2-mercaptoethanol, and centrifuged for 20 minutes at 18,000×g at 20° C., the resultant supernatant was adjusted to pH 6.4 with 2 N HCl, and centrifuged for 20 minutes at 18,000×g at 4° C. The precipitate was dispersed in distilled water, and ammonium sulfate was added to 100% saturation. After centrifugation at 11,000×g for 20 minutes at 4° C., the precipitate was dialyzed against distilled water and freeze-dried. Thus, the soybean protein was obtained.

(2) Removal of phytate

As pretreatment, the anion exchange resin (Amberlite IRA-410, manufactured by Organo Co., Tokyo, Japan) shown in the following Table 1 was washed with 1N HCl, 1N NaOH and 0.05 M Tris-HCl buffer solution (pH 7.4), and the soybean protein sample (0.2 w/v % solution) dissolved in 0.05 M Tris-HCl buffer solution (pH 7.4) was mixed with the anion exchange resin pretreated as above, and stirred at 4° C. for 3 hours. After filtering through cotton cloth, the filtrate was dialyzed against distilled water and freeze-dried.

The anion exchange resin was used in an amount of 5 g per 100 ml of a 0.2 w/v % soybean protein solution.

TABLE 1

| | Brand name | Exchange-group | Ion-exchange Capacity (gEg/l humid resin) |
|---|---|---|---|
| Example 1 | Amberlite IRA410 | —N$^+$(CH$_3$)$_2$'C$_2$H$_4$OH | 1.35 |
| Example 2 | Amberlite IRA400 | —N$^+$(CH$_3$)$_3$ | 1.4 |
| Example 3 | Amberlite IRA411S | —N$^+$(CH$_3$)$_2$'C$_2$H$_4$OH | 0.8 |
| Example 4 | Amberlite IRA458 | —N$^+$(CH$_3$)$_3$ | 1.25 |

(3) Deamidation treatment

The cation exchange resin (Amberlite IRC-50, manufactured by Organo Co., Tokyo, Japan) shown in the following Table 2 was washed with 1N HCl, 1N NaOH, and 0.05 M Tris-HCl buffer solution (pH 7.4), as pretreatment.

TABLE 2

| | Brand name | Exchange group | Ion-exchange Capacity (gEg/l humid resin) |
|---|---|---|---|
| Example 1 | Amberlite IRC50 | —COOH | 3.0 |
| Example 11 | Amberlite IRC718 | —N(CH$_2$COOH)$_2$ | 0.8 |
| Comparative Example 1 | Amberlite IR120B | —SO$_3$H | 1.9 |
| Comparative Example 2 | Amberlite XT1006 | —SO$_3$H | 2.4 |

The soybean protein sample wherein phytate was removed as mentioned above was dissolved in 0.05 M Tris/HCl buffer solution (pH 7.4) (so that the concentration might be 0.2 w/v % solution), then mixed with the cation exchange resin pretreated as above, and then was stirred at 4° C. for 6 hours.

After filtering with cotton cloth, the filtrate was dialyzed against distilled water and freeze-dried.

The cation exchange resin was used in an amount of 5 g per 100 ml of a 0.2 w/v % soybean protein solution.

Thus, the calcium absorption enhancing agent of the present invention was produced.

Examples 2–4

Calcium absorption enhancing agents were manufactured in accordance with the same method as the above except that Amberlite IRA-400 (Example 2), Amberlite IRA-411S (Example 3), and Amberlite IRA-458 (Example 4) each manufactured by Organo Co., Tokyo, Japan were respectively used instead of Amberlite IRA-410 in the treatment of removing phytate.

Ion exchange capacity and exchange groups of each of the anion exchange resins were shown in Table 1.

Examples 5–8

Calcium absorption enhancing agents were manufactured by the same method as Example 1 except that the treatment time of the treatment of removing phytate was 1 hour (Example 5), 6 hours (Example 6), 12 hours (Example 7), or 24 hours (Example 8).

Examples 9 and 10

Calcium absorption enhancing agents were manufactured in the same method as Example 1 except that the treatment time of the treatment of removing phytate was 1 hour, and an amount of the anion exchange resin to be used was 10 g (Example 9) or 25 g (Example 10).

Example 11

A calcium absorption enhancing agent was manufactured by the same method as Example 1 except that Amberlite IRC718 manufactured by Organo Co., Tokyo, Japan was used instead of Amberlite IRC-50 in the deamidation treatment.

Ion exchange capacity and exchange groups of Amberlite IRC718 were shown in Table 2.

Comparative Examples 1 and 2

Calcium absorption enhancing agents were manufactured by the same method as Example 1 except that Amberlite IR120B (Comparative Example 1), and Amberlite XT 1006 (Comparative Example 2), each manufactured by Organo Co., Tokyo, Japan were used respectively instead of Amberlite IRC-50 in the deamidation treatment.

Ion exchange capacity and exchange groups of each of the cation exchange resins were shown in Table 2.

Examples 12–15

Calcium absorption enhancing agents were manufactured by the same method as Example 1 except that the treatment time of the deamidation treatment was 1 hour (Example 12), 3 hours (Example 13), 12 hours (Example 14) or 24 hours (Example 15).

Examples 16–18

Calcium absorption enhancing agents were manufactured by the same method as Example 1 except that the amount of the weakly acidic cation exchange resin used for the deamidation treatment was 10 g (Example 16), 50 g (Example 17), or 100 g (Example 18).

Test Example 1: Measurement of Phytate Removal

Since most phosphorus in soybean exists as phytate, the amount of phosphorus was used as an index of phytate content. Each of the calcium absorption enhancing agents manufactured in Examples 1–10 were hydrolyzed with 6 N HCl under reduced pressure at 110° C. for 24 hours. The resultant hydrolyzate was allowed to pass through a glass filter. The filtrate was dried under reduced pressure, and 10 mg each of the dried samples (Examples 1–10) was dissolved in 10 ml of 0.2 M Tris-HCl buffer solution (pH 7.4). Calcium content and phosphorus content in each sample solution were measured with an inductively-coupled-plasma atomic emission spectroscopy (model M, SPECTRO Analytical Instruments, Kleve, Germany). For comparison, the content of phosphorus in soybean protein which was subjected to neither the treatment of removing phytate nor the amidation treatment (untreated soybean protein) was also measured.

Figure 1:
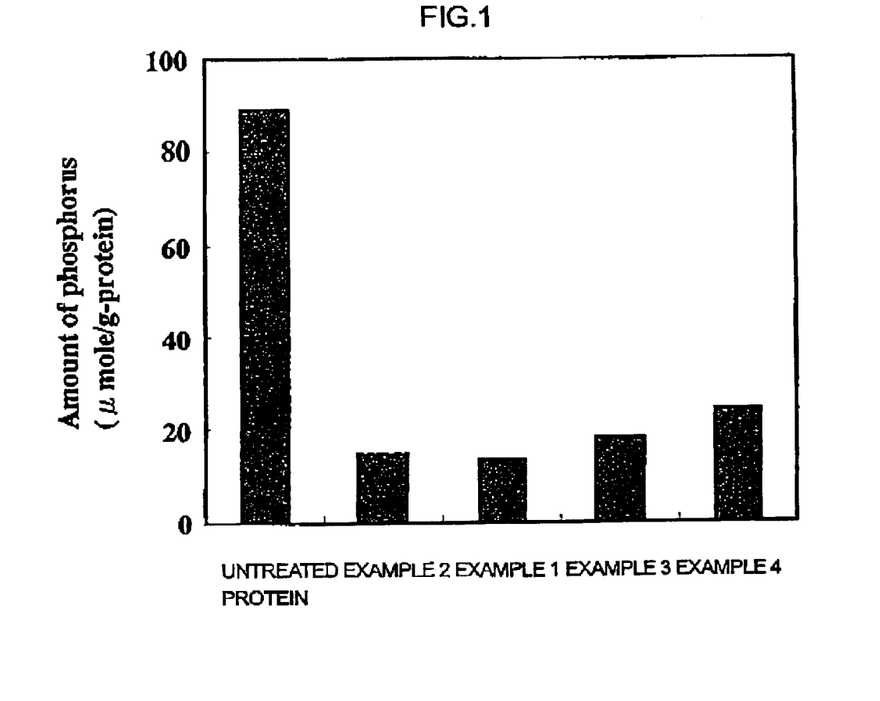
FIG. 1 is a graph showing the results of phytate removal as for the calcium absorption enhancing agents of examples of the present invention.

The results of measurement as for the calcium absorption enhancing agents of the above-mentioned Examples 1–4 and the untreated soybean protein were shown in FIG. 1.

Figure 2:
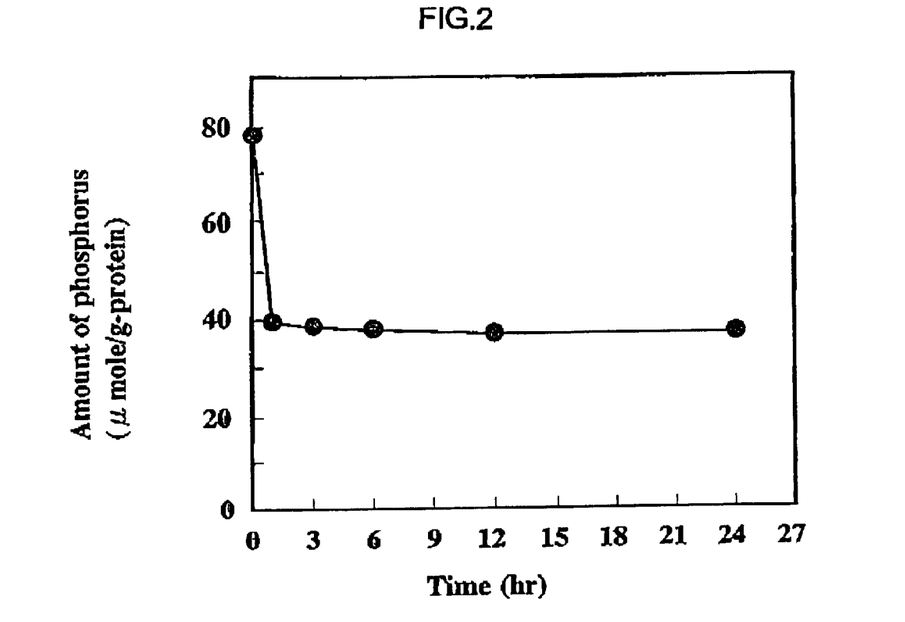
FIG. 2 is a graph showing the results of phytate removal as for the calcium absorption enhancing agents of examples of the present invention.

The results of measurement as for the calcium absorption enhancing agents of the above-mentioned Examples 1 and 5 to 8 and the untreated soybean protein were shown in FIG. 2.

Figure 3:
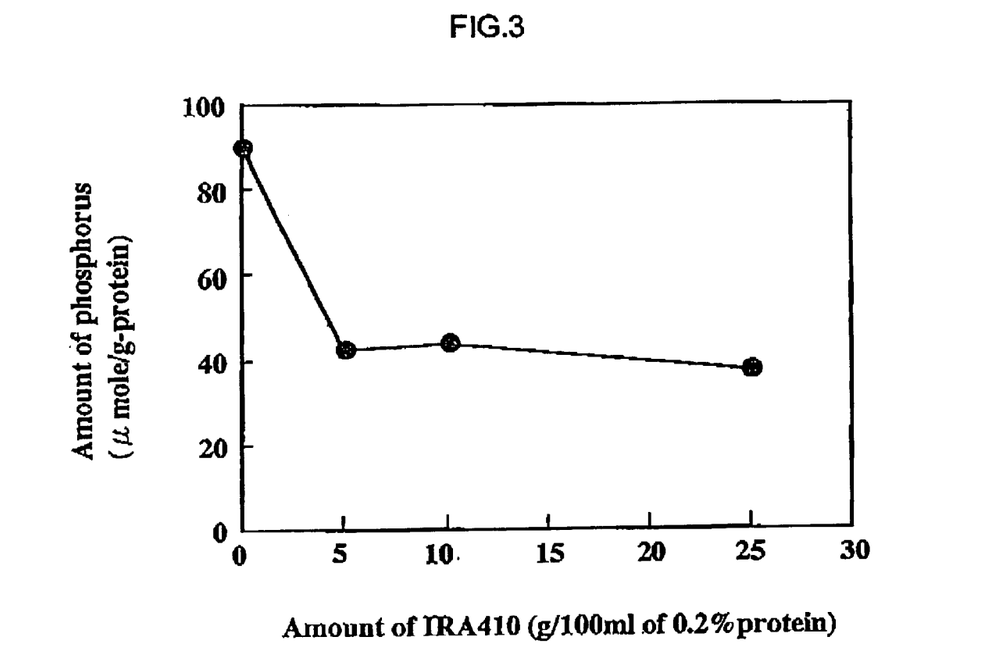
FIG. 3 is a graph showing the result of phytate removal as for the calcium absorption enhancing agents of examples of the present invention.

The results of measurement as for the calcium absorption enhancing agents of the above-mentioned Examples 1, 9, 10 and the untreated soybean protein were shown in FIG. 3.

Test Example 2: Measurement of Deamidation Amount

The amount of deamidation was measured as for the calcium absorption enhancing agents of the Examples 1, 11–18 and Comparative examples 1 and 2 as follows.

The total amount of acids amides of the protein was calculated by deamidating the above soybean protein which was not subjected to deamidation treatment, completely with HCl, and measuring the amount of generated ammonia (the total amount of acid amide).

Next, an amount of the remaining acid amide was calculated by deamidating the protein subjected to the deamidation treatment with the cation exchange resin, completely with HCl (the amount of the remaining acid amide).

The amount of the removed amide was calculated by the following formula.

The amount of the removed amide=the total amount of acid amide−the amount of the remaining acid amide.

The amount of generated ammonia was measured by a combination of Conway's micro-diffusion method and indophenol method. In a sealed vessel, ammonia released from the sample solution by a strong alkali ($K_2CO_3$) was absorbed into 0.5 ml of 1/100 N $H_2SO_4$. After incubating at 37° C. for 2 hours, 0.5 ml of the resultant ammonium sulfate solution was taken into a test tube cooled in ice-cold water, and 0.05 ml of 0.003 M $MnSO_4$, 1 ml of an alkaline phenol solution and 0.5 ml of NaClO were added. The test tube was immediately sealed with a cap, shaken and placed in boiling water for five minutes. The solution was then diluted with 10 ml of distilled water, and the absorbance of indophenol generated by the reaction was measured at 625 nm with a spectrophotometer (model UV-240, Shimadzu Corp. Tokyo, Japan). A calibration curve was made by using an ammonium sulfate solution with a known concentration.

Figure 4:
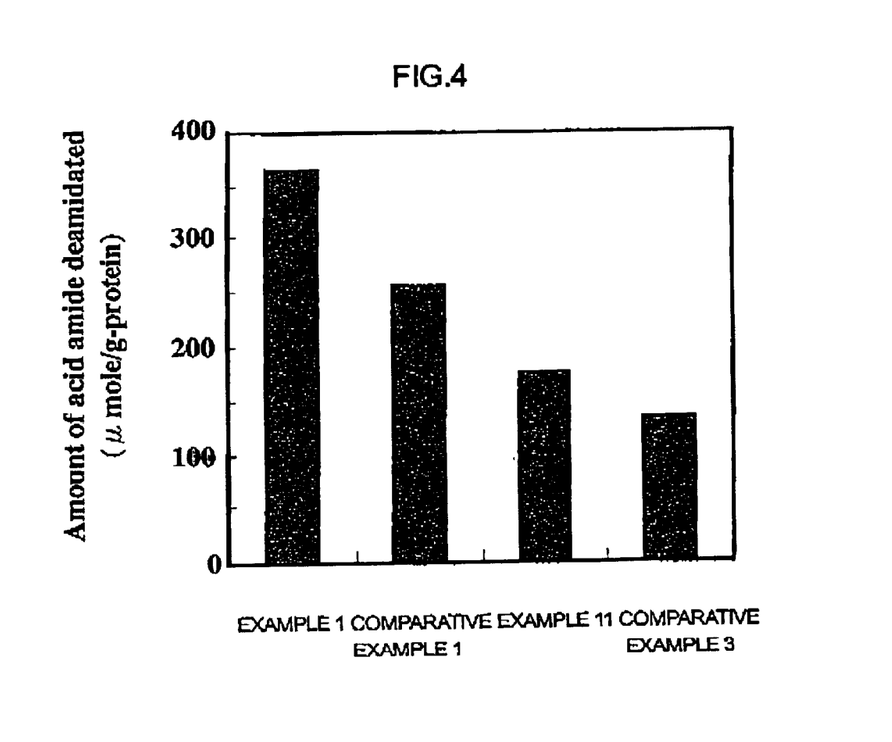
FIG. 4 is a graph showing the results of deamidation as for the calcium absorption enhancing agents of examples of the present invention and comparative examples.

The results measured as for the above-mentioned calcium absorption enhancing agents of Example 1, Example 11, and Comparative examples 1 and 2 are shown in FIG. 4.

Figure 5:
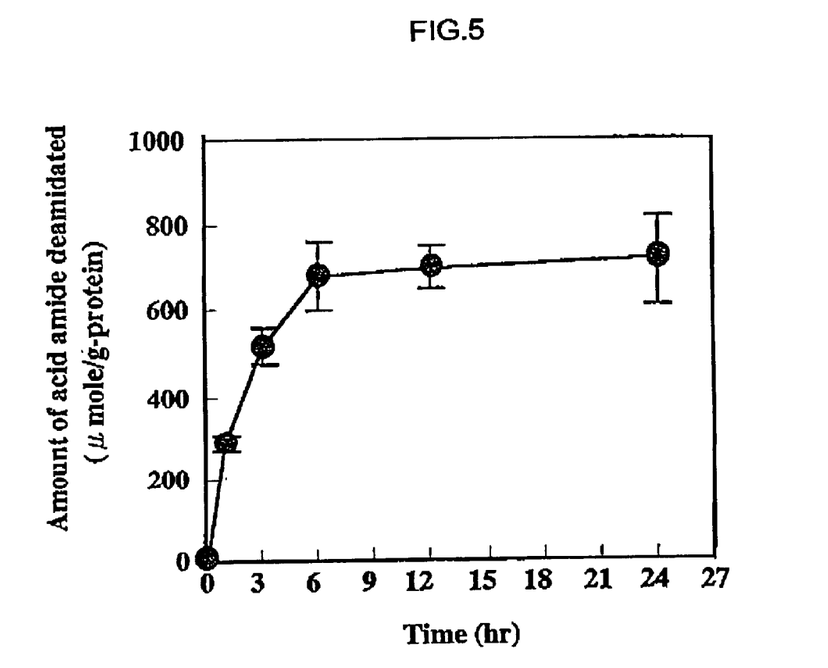
FIG. 5 is a graph showing the results of deamidation as for the calcium absorption enhancing agents of examples of the present invention.

The results measured as for the above-mentioned calcium absorption enhancing agents of Examples 1 and 12–15 are shown in FIG. 5.

Figure 6:
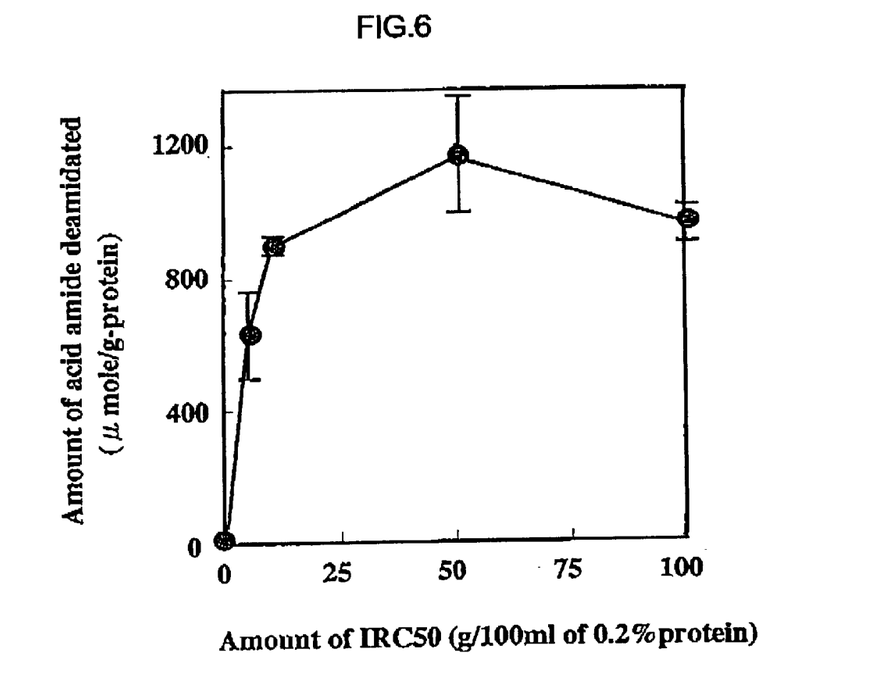
FIG. 6 is a graph showing the results of deamidation as for the calcium absorption enhancing agents of examples of the present invention.

The results measured as for the above-mentioned calcium absorption enhancing agents of Examples 1 and 16–18 are shown in FIG. 6.

Test Example 3: Evaluation of Calcium Binding Property

A calcium binding property was investigated as for the calcium absorption enhancing agent (Example 19) obtained by the same method as Example 1 except that calcium in the soybean protein extracted from the raw material soybean was removed in advance by the following method.

(Removal of Calcium)

The cation exchange resin (Amberlite XT1006, manufactured by Organo Co., Tokyo, Japan) was successively washed with 1N HCl, 1N NaOH, and a 0.05 M Tris-HCl buffer solution (pH 7.4). The soybean protein extracted in the Example 1 was dissolved in 100 ml of the 0.05 M Tris-HCl buffer solution (pH 7.4) so that the concentration might be 0.2 w/v %, then mixed with the above-mentioned pretreated cation exchange resin (5 g), and stirred for 15 minutes at 4° C. After filtered through a cotton cloth, the filtrate was dialyzed against distilled water and freeze-dried.

An amount of free calcium in the sample solution was measured using electric-potential-difference method. As shown in the following formula, the electromotive force (E) is related to the free calcium concentration (C).

$$E = E^{D°} + (RT/2F) \ln a = E^{D°} + (RT/2F)(\ln \gamma + \ln[C])$$

where $E^{D°}$ is a standard potential, R is a gas constant, T is an absolute temperature, F is a Faraday's constant, a is a calcium ionic activity and $\gamma$ is an activity coefficient.

The concentration of free calcium is measured at 25.0±0.5° C., using the ion meter (IM-40S, manufactured by TOA electronics) connected to a calcium ion-selective electrode (CA-135B, manufactured by TOA electronics, Japan) and to a double-junction reference electrode (HS-305DS, manufactured by TOA electronics). The ion meter was calibrated with 0 to $5 \times 10^{-4}$ M calcium chloride solutions. The concentration of the standard calcium chloride solution was taken as the free calcium ion concentration. All the solutions were prepared with a 0.2 M Tris-HCl buffer solution (pH 7.4). The pH is the same as the pH of the lower part of the small intestine where most calcium is absorbed.

The amount of bound calcium (AC) was calculated by subtracting the concentration of free calcium (C) from the total calcium concentration (Ct).

Figure 7:
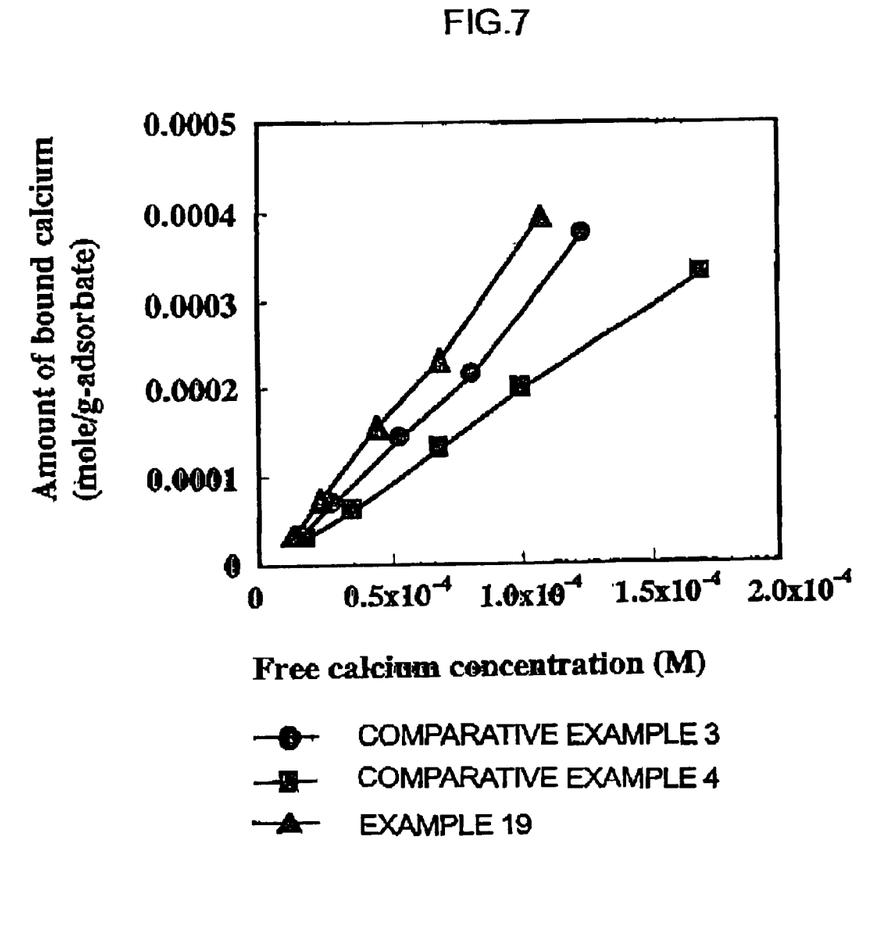
FIG. 7 is a graph showing the result of the calcium binding property of the calcium absorption enhancing agents of the examples of the present invention and comparative examples.

For comparison, the same tests were performed as for the calcium absorption enhancing agent manufactured by the same method as Example 1 except that calcium had been removed in advance by the above-mentioned method, and neither the phytate removing treatment nor the deamidation treatment was performed (Comparative example 3), and the calcium absorption enhancing agent manufactured by the same method as Example 1 except that calcium had been removed in advance by the above-mentioned method and the deamidation treatment was not performed (Comparative example 4). The results were shown in FIG. 7.

INDUSTRIAL APPLICABILITY

According to the present invention, an efficient calcium absorption enhancing agent can be obtained at low cost, since the calcium absorption enhancing agent of the present invention is obtained by removing phytic acid or its salt from vegetable protein and carrying out the deamidation of the acid amide group of the constituting amino acid using the weakly acidic cation exchange resin. Since the ion exchange resin used for manufacture is reproducible, manufacture cost can be further reduced, and is desirable also from a view point of saving resources.

Moreover, the calcium absorption enhancing agent obtained by the present invention is excellent in food processability, and can be applied to a wide range of food, while it has a high calcium absorption enhancing effect. Thereby, the amount of calcium ingestion can be increased irrespective of taste of a person, and health of Japanese people can be greatly improved.

What is claimed is:

1. A calcium absorption enhancing agent produced by subjecting a vegetable protein to at least a treatment of removing a phytate with an anion exchange resin and a deamidation treatment with a weakly acidic cation exchange resin.

2. The calcium absorption enhancing agent according to claim 1 wherein the above-mentioned vegetable protein is a soybean protein.

3. The calcium absorption enhancing agent according to claim 1 wherein the deamidation treatment with the weakly acidic cation exchange resin is conducted at a temperature in the range of 0–50° C.

4. The calcium absorption enhancing agent according to claim 2 wherein the deamidation treatment with the weakly acidic cation exchange resin is conducted at a temperature in the range of 0–50° C.

5. The calcium absorption enhancing agent according to claim 1 wherein the weakly acidic cation exchange resin has carboxyl groups as an exchange group.

6. The calcium absorption enhancing agent according to claim 2 wherein the weakly acidic cation exchange resin has carboxyl groups as an exchange group.

7. The calcium absorption enhancing agent according to claim 3 wherein the weakly acidic cation exchange resin has carboxyl groups as an exchange group.

8. The calcium absorption enhancing agent according to claim 4 wherein the weakly acidic cation exchange resin has carboxyl groups as an exchange group.

9. A method for producing a calcium absorption enhancing agent wherein a vegetable protein extracted from a plant is subjected to at least a treatment of removing a phytate with an anion exchange resin and a deamidation treatment with a weakly acidic cation exchange resin.

10. The method for production according to claim 9 wherein the deamidation treatment with the weakly acidic cation exchange resin is conducted at a temperature in the range of 0–50° C.

11. A calcium enriched food which contains the calcium absorption enhancing agent according to claim 1.

12. A calcium enriched food which contains the calcium absorption enhancing agent according to claim 4.

13. A calcium enriched food which contains the calcium absorption enhancing agent according to claim 6.

14. A nutrition composition for calcium enrichment which contains the calcium absorption enhancing agent according to claim 1.

15. A nutrition composition for calcium enrichment which contains the calcium absorption enhancing agent according to claim 4.

16. A nutrition composition for calcium enrichment which contains the calcium absorption enhancing agent according to claim 6.

17. A pharmaceutical preparation which contains the calcium absorption enhancing agent according to claim 1.

18. A pharmaceutical preparation which contains the calcium absorption enhancing agent according to claim 4.

19. A pharmaceutical preparation which contains the calcium absorption enhancing agent according to claim 6.

20. The calcium absorption enhancing agent according to claim 1, wherein the weakly acidic cationic exchange resin comprises at least one ion exchange group selected from the group consisting of —COOH, —OCH$_2$COOH, —N(CH$_2$COOH)$_2$, and —CH$_2$N(CH$_2$COOH)$_2$.

21. The calcium absorption enhancing agent according to claim 20, wherein the weakly acidic cationic exchange resin comprises at least one ion exchange group selected from the group consisting of —COOH and —N(CH$_2$COOH)$_2$.

22. The calcium absorption enhancing agent according to claim 1, wherein the weakly acidic cationic exchange resin has an ion exchange capacity in the range of from 0.5 gEq/l to 5 gEq/l of humid resin.

23. The method according to claim 9, wherein the deamidation treatment with a weakly acidic cationic exchange resin comprises treatment with a weakly acidic cationic exchange resin having at least one ion exchange group selected from the group consisting of —COOH, —OCH$_2$COOH, —N(CH$_2$COOH)$_2$, and —CH$_2$N(CH$_2$COOH)$_2$.

24. The method according to claim 23, wherein the deamidation treatment with a weakly acidic cationic exchange resin comprises treatment a weakly acidic cationic exchange resin having at least one ion exchange group selected from the group consisting of —COOH and —N(CH$_2$COOH)$_2$.

25. The method according to claim 9, wherein the deamidation treatment with a weakly acidic cationic exchange resin comprises treatment with a weakly acidic cationic exchange resin having an ion exchange capacity in the range of from 0.5 gEq/l to 5 gEq/l of humid resin.

26. A calcium enriched food which contains the calcium absorption enhancing agent according to claim 20.

27. A calcium enriched food which contains the calcium absorption enhancing agent according to claim 21.

28. A calcium enriched food which contains the calcium absorption enhancing agent according to claim 22.

29. A nutrition composition for calcium enrichment which contains the calcium absorption enhancing agent according to claim 20.

30. A nutrition composition for calcium enrichment which contains the calcium absorption enhancing agent according to claim 21.

31. A nutrition composition for calcium enrichment which contains the calcium absorption enhancing agent according to claim 22.

32. A pharmaceutical preparation which contains the calcium absorption enhancing agent according to claim 20.

33. A pharmaceutical preparation which contains the calcium absorption enhancing agent according to claim 21.

34. A pharmaceutical preparation which contains the calcium absorption enhancing agent according to claim 22.

* * * * *

UNITED STATES PATENT AND TRADEMARK OFFICE
CERTIFICATE OF CORRECTION

PATENT NO.   : 6,656,511 B1
DATED        : December 2, 2003
INVENTOR(S)  : Hitomi Kumagai It is certified that error appears in the above-identified patent and that said Letters Patent is hereby corrected as shown below:

<u>Title page, Item [54], and Column 1, line 1,</u>
Title, should read -- A CALCIUM ABSORPTION ENHANCING AGENT --

Signed and Sealed this

Twenty-seventh Day of April, 2004

JON W. DUDAS
*Acting Director of the United States Patent and Trademark Office*